United States Patent [19]

Muir et al.

[11] Patent Number: 5,891,435
[45] Date of Patent: Apr. 6, 1999

[54] METHODS AND COMPOSITIONS FOR DELAYING OR PREVENTING THE ONSET OF AUTOIMMUNE DISEASE

[75] Inventors: Andrew Muir, Gainesville; Noel K. Maclaren, Archer, both of Fla.

[73] Assignee: Research Corporation Technologies, Inc., Tucson, Ariz.

[21] Appl. No.: 48,979

[22] Filed: Apr. 16, 1993

[51] Int. Cl.$^6$ .................................................. A61K 38/28
[52] U.S. Cl. .................................. 424/185.1; 424/198.1; 530/300; 530/350; 530/399
[58] Field of Search ................................ 424/88, 89, 92, 424/93 A, 184.1, 185.1, 198.1; 514/2; 435/69.3, 235.1, 252.3, 320.1; 530/350, 826, 868

[56] References Cited

U.S. PATENT DOCUMENTS

| | | | |
|---|---|---|---|
| 4,338,306 | 7/1982 | Kitao et al. | 424/178 |
| 4,464,363 | 8/1984 | Higuchi et al. | 424/232 |
| 4,650,785 | 3/1987 | Toyoshima et al. | 514/3 |
| 4,789,660 | 12/1988 | Enever et al. | 514/4 |
| 5,512,447 | 4/1996 | Baekkeskov et al. | 435/7.4 |
| 5,691,448 | 11/1997 | Baekkeskov et al. | 530/350 |

FOREIGN PATENT DOCUMENTS

| | | | |
|---|---|---|---|
| 0 055 885 | 7/1982 | European Pat. Off. | A61K 37/26 |
| 4-506297 | of 0000 | Japan . | |
| WO9101333 | 7/1990 | WIPO | C07K 13/00 |
| WO 90/15873 | 12/1990 | WIPO | C12N 15/74 |
| WO9112816 | 3/1991 | WIPO | A61K 37/20 |
| WO9115225 | 10/1991 | WIPO | A61K 37/02 |
| WO9206704 | 10/1991 | WIPO | A61K 37/26 |
| WO 95/24216 | 9/1995 | WIPO | A61K 39/39 |

OTHER PUBLICATIONS

Gilman, A. et al. (ed), Tha Pharmaceutical Basis of Therapeutics, 8th edition, pp. 1463–1484, 1990.

Atkinson, M. A. et al., J. clin. Invest. 92:1608–1616 (1993), Islet cell autoantigens in insulin–dependent diabetes.

Michael, J. G. et la., Immunological Invest. 18:1049–1054 (1989), The role of digestive enzymes in orally induced immune tolerance.

Paul, W.F. (ed.), *Fundamental Immunology* (1993), pp. 714–720 and 1067–1069. Raven Press, New York.

Cohen, I.R. et al., Dialog abstract 0902938, "Immunization to insulin generates antiidotypes that behave as antibodies to the insulin hormone receptor and cause diabetes mellitus".

Freytag, G. et al., Dialog abstract 542248, "Latent diabetes mellitus in guinea pigs induced by active immunization against bovine insulin".

Kloeppel, G. et al., Dialog abstract 1612079, Immune insulitis and manifest diabetes mellitus studies on the course of immune insulitis and the induction of diabetes mellitus in rabbits immunized with insulin.

Muir et al. Abstract entitled "Insulin–Specific Immunotherapy Ameliorates Diabetes in Nonobese Diabetic Mice" *Journal of the American Diabetes Association, Supplement 1*, (Program of the 52nd Annual Meeting of the American Diabetes Association, held Jun. 20–23, 1992).

Sokrut et al. (1991) *Database WPI, Section Ch, Week 9201, Derwent Publications Ltd., London, Abstract AN 92–005453 and SU1624511.*

Melez, K.A. et al., "Immune Abnormalities in the Diabetic New Zealand Obese (NZO) Mouse: Insulin Treatment Partially Suppresses Splenic Hyperactivity Measured by Flow Cytometric Analysis"; *Clinical Immunology and Immunopathology* (1985) 36, 110–119.

Panicali and Paoletti, "Construction of poxviruses as cloning vectors: Insertion of the thymidine kinase gene from herpes simplex virus into the DNA of infectious vaccinia virus"; *Proc. Natl. Acad. Sci. USA* (1982) 79, 4927–4931.

Ziegler, Anette G., Ralph Ziegler, Pnin Varki, Richard A. Jackson, J. Stuart Soeldner, and George S. Eisenbarth (1989) "Life–Table Analysis of Progression to Diabetes of Anti–Insulin Autoantibody–Positive Relatives of Individuals With Type 1 Diabetes" Diabetes 38:1320–1325.

Vardi, P., A.G. Ziegler, J.H. Mathews, S. Dib, R.J. Keller, A.T. Ricker, J.I. Wolfsdorf, R.D. Herskowitz, A. Rabizadeh, G.S. Eisenbarth, J.S. Soeldner (1988) "Concentration of InsulinAutoantibodies at Onset of Type 1 Diabetes: Inverse Log–Linear Correlation with Age" Diabetes Care 11(9):736–739.

Atkinson, Mark A., Noel K. Maclaren, and Roberto Luchetta (1990) "Insulitis and Diabetes in NOD Mice Reduced by Prophylactic Insulin Therapy" Diabetes 39:933–937.

Steiner et al. (1989) "Chemistry and Biosynthesis of Pancreatic Protein Hormones," In Endocrinology, DeGroot et al., Eds., W.B. Saunder Company, pp. 1263–1289.

Palmer, et al. (1983) "Insulin Antibodies in Insulin–Dependent Diabetics Before Insulin Treatment," Science, vol. 222:1337–1339.

Aaen et al. (1990) "Dependence of Antigen Expression on Functional State of B–Cells," Diabetes, vol. 39:697–701.

Kampe et al., "High–Glucose Stimulation of 64,000–$M_r$ Islet Cell Autoantigen Expression," (1989) Diabetes, vol. 38:1326–1328.

Jacob et al., "Prevention of Diabetes in Nonobese Diabetic Mice by Tumor Necrosis Factor (TNF): Similarities between TNF–a and Interleukin 1," (1990) Proc. Natl. Acad. Sci. USA, vol. 87:968–972.

Sadelain et al., "Prevention of Type I Diabetes in NOD Mice by Adjuvant Immunotherapy," (1990) Diabetes, vol. 39:583–589.

Like et al., Influence of Environmental Viral Agents on Frequncy and Tempo of Diabetes Mellitus in BB/Wor Rats, (1991) Diabetes, vol. 40:259–262.

(List continued on next page.)

*Primary Examiner*—Thomas M. Cunningham
*Attorney, Agent, or Firm*—Greenlee, Winner and Sullivan, PC

[57] ABSTRACT

The subject invention concerns compositions and methods useful for the prevention or amelioration of autoimmune diseases. Specifically exemplified are compositions and methods useful in immunizing to prevent insulin dependent diabetes. In a preferred embodiment, diabetes is prevented by the parenteral administration of a composition comprising specific antigenic peptides of insulin and further comprising incomplete Fruend's adjuvant.

8 Claims, 1 Drawing Sheet

OTHER PUBLICATIONS

Steinman, Lawrence (1990), "Development of Antigen–specific Therapies for Autoimmune Disease," Mol. Biol. Med. 7:333–339.

Offner, H., G.A. hashim, A.A. Vandenbark, "T Cell Receptor Peptide Therapy Triggers Autoregulation of Experimental Encephalomyclitis" (1991) Science, vol. 251:430–432.

Kim, C., K.A. Siminovitch, A. Orchi, "Reduction of Lupus, nephritis in MRL/lpr Mice by a Bacterial Superantigen Treatment," (1991) J. Exp. med. 174:1431–1437.

Silverman, et al., "Enterically induced regulation of Systemic Immune Responses," vol. 131:2651–2661.

Peng, H.J., M.W. Turner, S. Strobel, "The Generation Of a Tolerogen After the Ingestion of Ovalbumin is Time–dependent and Unrelated to Serum levels of Immunoreactive Antigen," (1990) Clin. Exp. Immunol, vol. 81:510–515.

Michael, J. Gabriel, "The Role of Digestive Enzymes in orally Induced Immune Tolerance," (1989) Immune Invest. 18:1049–1054.

Kitamura et al., "Contrasuppressor Cells That Break Oral Tolerance Are Antigen–Specific T Cells Distinct From T helper (L3T4$^+$), T Suppressor (Lyt–2$^+$), and B Cells," (1987) J. Immunol. 139:3251–3259.

Michalek et al., "Lipopolysaccharide (LPS) Regulation Of The Immune Response: LPS Influence On Oral Tolerance Induction," (1982) The Journal of Immunology, vol. 128:1992–1998.

Mowat, A.M. et al., "Divergent Effects of Bacterial Lipopolysaccharide on Immunity to Orally Administered protein and Particulate Antigens in Mice," (1986) Immunology, vol. 58:677–683.

Nagler–Anderson, Cathryn et al., "Suppression of Type II Collagen–induced Arthritis by Intragastric Administration of Soluble Type II Collagen," (1986) Proc. Natl. Acad. Sci. USA, vol. 83:7443–7446.

Gesualdo, Loreto et al., "Defective Oral Tolerance Promotes Nephritogenesis In Experimental IgA Nephropathy Induced By oral Immunization," (1990) J. Immunol. 145:3684–3691.

Miller, et al., "Heterogeneity of Oral Tolerance Defects in Autoimmune Mice," (1984) Clin. Immunol. Immunopathol. 31:231–240.

Zhang et al., "Suppression of Diabetes in Nonobese Diabetic Mice by Oral Administration of Porcine Insulin," (1991) Proc. Natl. Acad. Sci. USA, vol. 88:10252–10256.

W. F. Paul (ed), *Fundamental Immunology*, 3rd edition (1993), pp. 1067–1069.

Paoletti, E., et al., P.N.A.S. (USA) 81:193–197 (Jan., 1984), "Construction of live vaccines using genetically engineered poxviruses . . . ".

*Robbins Pathological Basis of Disease*(R.S. Cotran, et al., eds.), 4th edition (1989), pp. 994–1001.

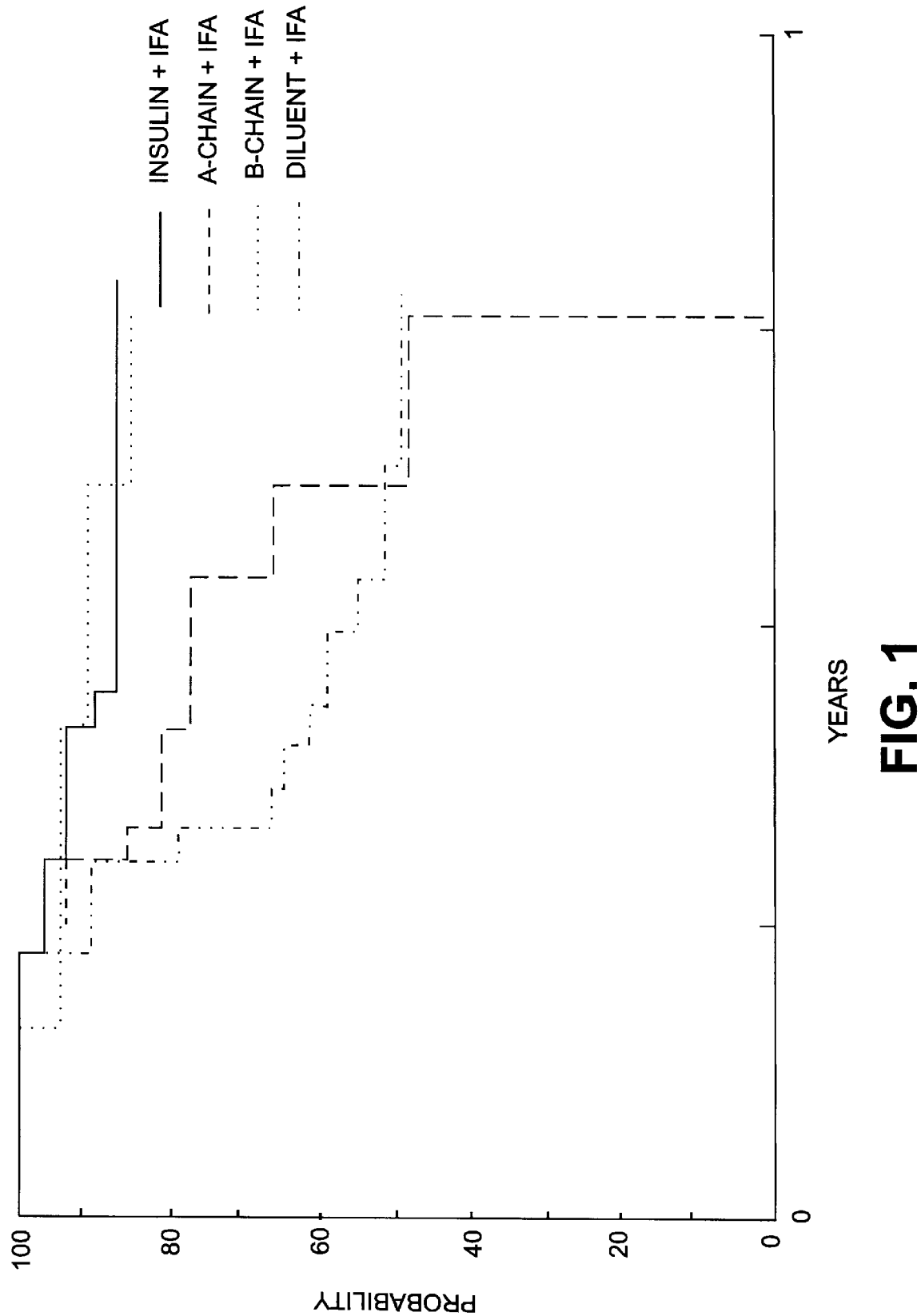

METHODS AND COMPOSITIONS FOR DELAYING OR PREVENTING THE ONSET OF AUTOIMMUNE DISEASE This invention was made with government support under NIH Grant Nos. PO1DK39079 and RO1HD19469-09 and the Juvenile Diabetes Foundation, International Grant No. 1921523. The government has certain rights in this invention.

BACKGROUND OF THE INVENTION

Autoimmune diseases are characterized by an abnormal immune response (involving either immune system cells or antibodies) directed against normal autologous (self) tissues. Autoimmune diseases afflict huge numbers of individuals throughout the world.

A normal immune system has the capacity to identify and destroy a large variety of foreign invader organisms such as bacteria and viruses. Remarkably, a normal immune system can readily distinguish foreign substances from self, and thereby is able to react vigorously against potentially pathogenic entities from the environment without harming the host's own cells.

The immune system's non-reactivity to self is termed immunological tolerance. In pathological situations, immunological tolerance to a wide variety of self substances is broken, resulting in an autoimmune response to self. If of an appropriate nature and of sufficient severity and duration, the anti-self response will result in an autoimmune disease. In certain autoimmune diseases, specific elements of the immune system predominate in mediating the pathogenic process, while in other autoimmune diseases, all of the components of the immune system cooperate to produce disease. Antibodies are considered to play the major causal roles in diseases such as systemic lupus erythematosus, myasthenia gravis and Graves' disease, while cellular immune mechanisms are believed to be those primarily involved in multiple sclerosis (MS) and insulin dependent diabetes (IDD).

Whereas susceptibility to autoimmune diseases may be inherited through the defective actions of multiple genes, indirect evidence exists to suggest that an interaction with a foreign substance from the environment may also be necessary to induce the pathogenic process that results in disease. One explanation for this is that immunization with the foreign inductive chemical induces a cross-reactive response to self through molecular mimicry or chemical similarity. However, once the autoimmune process has been initiated, other secondary immunizing events involving other self antigens typically occur through the release of intracellular constituents in forms not normally encountered by the immune system. Targeted organs thus become damaged through the combination of all of these events, which will lead to the appearance of a clinically recognized disorder only when the disease process has progressed to result in the ablation of large numbers of tissue cells so targeted.

A number of strategies have been used or proposed to suppress autoimmune diseases, most notably drugs, such as cyclophosphamide, cyclosporin A, methotrexate, and Imuran (azathioprine). Steroid compounds, such as prednisone and methylprednisolone, are also employed in many instances. These drugs have limited long term efficacy against both cell- and antibody-mediated autoimmune diseases. Use of such drugs is limited by virtue of their toxic side effects which include "global" immunosuppression. Prolonged treatment with these drugs inhibits the normal protective immune response to pathogenic microorganisms, thereby increasing the risk of infections. A further drawback is that immune-mediated elimination of aberrant cells is impaired and there is, thus, an increased risk that malignancies will develop in patients receiving prolonged global immunosuppression.

The self substances, or autoantigens, which are the targets of autoimmune responses are most often protein products unique to the targeted cells (e.g., hormones such as insulin in IDD); particular enzymes unique to the specialized function of targeted cells (e.g., glutamic acid decarboxylase or GAD in IDD, or 21 hydroxylase in Addison's disease); specialized cell specific receptor molecules (e.g. the thyroid stimulating hormone or TSH receptor in Graves' disease or acetylcholine receptors in the neuromuscular junctions in myasthenia gravis); and/or structural constituents of the targeted cells or tissues (e.g., beta cell sialo-glycoconjugate in IDD). Prior to the current invention, immunization with autoantigens has been used as a means to induce autoimmune disease in experimental animals. For example, the administration of myelin basic protein (MBP) has been used as a means to induce EAE (a model for MS) in mice.

The methods and compositions of the subject invention are specifically exemplified with regard to the prevention of IDD. However, as discussed more fully herein, the principles discovered by applicants for preventing diabetes are broadly applicable to a variety of known autoimmune conditions as well as to autoimmune conditions which may be identified in the future. Known autoimmune disorders include diabetes, multiple sclerosis, autoimmune uveitis, rheumatoid arthritis, Addison's disease, thyroiditis, atrophic gastritis, myasthenia gravis, idiopathic thrombocytopenic purpura, hemolytic anemia, systemic lupus erythematosus, primary billary cirrhosis, Wegener's granulomatosis, polyarteritis nodosa, and inflammatory bowel disease. Because the subject invention is specifically exemplified with regard to diabetes, a detailed background of diabetes is provided below.

Insulin dependent diabetes. Diabetes mellitus comprises a group of diseases that result in elevations of blood glucose levels because of relative to absolute deficiencies in the pancreatic hormone, insulin. Insulin is secreted into the blood when food is ingested and has its major actions in directing the absorbed nutrients into body stores. Diabetes is a major public health problem affecting at least 5 and as many as 10 million Americans. The prevalence of the most severe form of IDD is 1 in 300 in the United States. In 1991, the direct health care costs attributable to diabetes care in the United States exceeded $20 billion, with as much as twice this figure in additional indirect costs, such as for loss of productivity (Bransome and Edwin [1992] *Diabetes Care* 15:1–5).

Chronic elevation of blood glucose levels is the most obvious metabolic effect in diabetes and is associated with progressive damage to blood vessels. This leads to heart attacks, strokes, blindness, peripheral nerve dysfunction, and kidney failure. The frequency and severity of diabetes related complications are greatest in the insulin dependent form of the disease, in which an immunological destruction of the pancreatic insulin-secreting beta cells occurs. The high rate of irreversible complications in IDD occurs despite the availability of insulin replacement through injections given 1–4 times daily.

Insulin, as well as other pancreatic hormones, are well known and characterized. See, for example, Steiner et al. (1989) "Chemistry and Biosynthesis of Pancreatic Protein Hormones," In *Endocrinology*, DeGroot et al., Eds., W. B. Saunders Company, pp. 1263–1289. As described in Steiner et al., the amino acid sequence of insulin is highly conserved across a number of species, including human, monkey, porcine, and bovine. Although insulin is well known for its association with diabetes, there are a number of other proteins which are also associated with the pancreas or diabetes. These other proteins include glucagon and glutamic acid decarboxylase (GAD).

Through the research efforts of ourselves and others, IDD has proved itself to be predictable both in unaffected relatives of patients with IDD, as well as in persons from the general population. A predisposition to develop clinical diabetes can be determined through several different tests. For example, genetic susceptibility to diabetes has become increasingly definable through the use of molecular biological means usually from DNA samples obtained from peripheral blood. One major gene involved in the inherited susceptibility to IDD is that located at the HLA-DQ locus. It is currently possible to identify risks varying from essentially none to those as high as 70 fold above those without the genetic genotype. In families, a genetic risk as high as 1 in 4 can be estimated for unaffected siblings just through identification of HLA haplotypes shared with the affected proband.

Persons who have just developed IDD or are in process of developing IDD have a number of disease specific autoantibodies in their blood. Such autoantibodies include those to islet cell antigens (ICA), to beta cell specific proteins of 64 kDa (now believed to be the lower molecular isoform of glutamic acid decarboxylase [$GAD_{65}$]) to native insulin and proinsulin, and to a number of more minor determinants such as carboxypeptidase-H and heat shock proteins belonging to the hsp-60 family.

Insulin autoantibodies (IAA) are observed in untreated, newly diagnosed IDD patients (Palmer et al. [1983] *Science* 222:1337–1339) as well as in unaffected relatives of diabetic probands. Whereas autoimmunity to insulin could directly cause β-cell damage, interfere with the action of endogenous insulin, or have both effects, some investigators suggested that IAA reflect the rate of islet cell destruction and thus act merely as reporters of aggressive islet directed autoimmunity (Ziegler et al. [1989] *Diabetes* 38:1320–1325; Vardi [1988] *Diabetes Care* 11:736–739).

The non-obese diabetic (NOD) mouse is a useful animal model for human IDD. Analysis of the NOD mouse provides important insights into the sequence of pathogenic events, which leads to an understanding of the nature of the target islet cell autoantigens involved in the autoimmunological process. Previous studies from our laboratory have demonstrated that an extended prophylactic course of daily, subcutaneous injections of porcine insulin protected NOD mice from both hyperglycemia and islet infiltration by mononuclear leukocytes (insulitis) (Atkinson et al. [1990] *Diabetes* 39:933–937). Such treatment may relieve the pancreatic β-cells of metabolic demands on them and thus induce a state of "β-cell rest." This quiescent state may be associated with diminished expression of many islet factors, including those that may serve as potential autoantigens at the cell surface (Aaen et al. [1990] *Diabetes* 39:697–701; Kämpe et al. [1989] *Diabetes* 38:1326–1328). Non-specific immunostimulation caused by cytokine (Jacob et al. [1990] *Proc. Natl Acad. Sci. USA* 87:968–972) or adjuvant (Sadelain et al. [1990] *Diabetes* 39:583–589) treatments, or environmental microbes have been implicated in other protocols of IDD prevention (Like et al. [1991] *Diabetes* 40:259–262). An enhanced understanding of the pathogenic role of insulin autoimmunity in IDD is clearly required.

There have been reports of efforts to induce antigen-specific immunoregulation to ameliorate autoimmune diseases (Steinman, L. [1990] *Mol. Biol. Med.* 7:333–339). For example, various methods have been employed to induce antigen-specific suppression of experimental allergic encephalomyelitis (EAE) (PCT application WO 91/15225). Recently, several novel immunological approaches have been explored relevant to autoimmune diseases such as EAE in mice and rats and lupus nephritis in MRL/lpr mice. Many have been directed toward blocking the function of the effector $CD4^+$ T cell which has been shown to exhibit $V_\beta$ isotype restriction in EAE. These approaches have included the use of anti-TCR antibodies (Acha-Orbea et al., supra), synthetic TCR peptides (Offner, H., G. A. Hashim, A. A. Vandenbark [1991] *Science* 251:430–432) and superantigen treatment (Kim, C., K. A. Siminovitch, A. Ochi [1991] *J. Exp. Med.* 174:1431–1437). The tolerogenic effects of intragastric antigens administration are also well described (Silverman et al. [1983] *J.Immunol.* 131:2651–2661; Peng et al. [1990] *Clin. Exp. Immunol.* 81:510–515; Michael [1989] *Immune Invest.* 18:1049–1054; Kitamura et al. [1987] *J. Immunol.* 139:3251–3259; Michalek et al. [1982] *J.Immunol.* 128:1992–1998; Mowat, A. M. et al. [1986] *Immunol.* 58:677–683; PCT applications WO 91/12816, WO 91/01333; WO 92/06704). Nagler-Anderson et al. ([1986] *Proc. Natl. Acad. Sci. USA* 83:7443–7446) describe the oral administration of collagen-induced arthritis in a mouse model. Deficiencies in this ability have been reported in several experimental mouse models of autoimmune diseases (Gesualdo et al. [1990] *J.Immunol.* 145:3684–3691; Miller et al. [1984] *Clin. Immunol. Immunopathol.* 31:231–240).

Zhang et al. observed a beneficial response to oral insulin (Zhang et al. [1991] *Proc. Natl. Acad. Sci. USA* 88:10252–10256) and further demonstrated in co-transfer studies that splenocytes from insulin-fed NOD mice prevented the adoptive transfer of diabetes by splenocytes from untreated, diabetic mice to irradiated recipients.

Our current invention provides the means for the first time to prevent the disease process from becoming established in the genetically predisposed, or otherwise in progressing once initiated as identifiable by autoantibodies, through a novel treatment that is akin to vaccination to self proteins important to the pathogenic process underlying IDD.

BRIEF SUMMARY OF THE INVENTION

The subject invention concerns unique compositions and methods for the prevention or early amelioration of autoimmune diseases. Specifically exemplified is a vaccination procedure to prevent or ameliorate insulin dependent, or Type 1, diabetes (IDD). This procedure is particularly advantageous when used to vaccinate persons found to be at genetic risk for, or in the process of, developing an autoimmune disease such as IDD. In the case of IDD, the vaccination procedure of the subject invention effectively blocks or immunologically overrides the autoimmune reaction that causes destruction of the cells of the pancreas that secrete insulin.

The immunization procedure of the subject invention can be applied to a number of immunological diseases in which there is a loss of function of, or injury to, a particular tissue of the body and for which there is an understanding of the targeted body constituents. Other autoimmune diseases for which the principles of the subject invention are applicable include, but are not limited to, multiple sclerosis, autoimmune uveitis, rheumatoid arthritis, Addison's disease, thyroiditis, Graves' disease, atrophic gastritis, myasthenia gravis, idiopathic thrombocytopenic purpura, hemolytic anemia, systemic lupus erythematosus, primary biliary cirrhosis, Wegener's granulomatosis, polyarteritis nodosa, and inflammatory bowel disease. A primary principle of the vaccination methods of the subject invention is that the antigen used to immunize is one that is targeted by the immunological disease or else is one uniquely present in the particular body tissues that become damaged by the pathological immune response. In the case of IDD, the antigen used to vaccinate can be an insulin antigen, glucagon, or $GAD_{65}$. In a preferred embodiment, we have discovered that the onset of IDD can be prevented or delayed by vaccination with the B chain, or a B chain peptide, of the insulin molecule.

As specifically described herein, we have induced an IDD resistant state in NOD mice by administering insulin subcutaneously with an appropriate adjuvant. We found that the incidence and severity of insulitis were little affected, or actually increased, by this procedure. Also, antibodies to insulin were stimulated by immunization with insulin in incomplete Freund's adjuvant (IFA). Despite these immunological responses which have previously been associated with the pathogenesis or disease progression of diabetes, strong protection for diabetes was achieved.

Subcutaneous immunization with the B chain of insulin, but not the hormone's A chain, reproduced the protective effect of insulin, suggesting the existence of an immunodominant epitope on the B chain. Thus, in a preferred embodiment, the vaccination strategy of the subject invention is particularly advantageous as applied to IDD because metabolically inactive insulin fragments can be used.

The protective effect achieved by the methods of the subject invention is apparently cell-mediated, since protection from IDD was induced by the infusion of splenocytes from acutely diabetic mice donors transferred to irradiated NOD mice recipients by the co-infusion of splenocytes harvested from B chain treated mice.

The immunization method of the subject invention obviates the need for daily insulin therapy, the need for repeated blood glucose monitoring, and the restrictions of diet and exercise imposed upon all patients with IDD receiving insulin replacement therapy. Further, and most importantly, the complications of IDD, which are directly attributable to the duration and severity of overt diabetes and hyperglycemia, will be inhibited. Those who would be likely to benefit most from insulin vaccination therapy would be those with a high genetic risk profile such as a five-fold and above risk as determined by HLA and/or other genotyping studies, as well as those found to have a high predictive profile as determined through specific autoantibody analyses, e.g., $GAD_{65}$ autoantibodies.

Individuals afflicted with other autoimmune conditions that have specifically localized targets such as myasthenia gravis, anemia, thrombocytopenia, rheumatoid arthritis, or other collagen-vascular diseases may benefit from similar immunization therapies with disease- or target-specific antigens.

BRIEF DESCRIPTION OF THE DRAWINGS

FIG. 1 depicts the effect of administering subcutaneous insulin peptides in IFA to NOD mice. The curve shows the percentage of non-diabetic mice among NOD mice who received IFA suspensions containing either insulin diluent, regular insulin, insulin A chain, or insulin B chain. Immunization with insulin B chain alone provided protection equal or superior to that conferred by intact insulin.

BRIEF DESCRIPTION OF THE SEQUENCES

SEQ ID NO. 1 is an 11-amino acid peptide on the beta chain of porcine insulin.

SEQ ID NO. 2 is a 9-amino acid peptide on the beta chain of porcine insulin.

DETAILED DISCLOSURE OF THE INVENTION

The subject invention concerns a new, clinically important, immunomodulating therapy that selectively inhibits destructive immune responses without inducing generalized immunosuppression replete with its inherent side effects. The treatment procedures of the subject invention represent an important advance in the care of patients suffering from, or predisposed to, autoimmune disorders. These disorders are a disparate collection of human diseases that have in common the failure of the immune system to recognize a tissue, organ or cellular component of the body as self. As the result of these pathological processes, self cells targeted for attack by the immune system become dysfunctional, destroyed with permanent loss of normal biological activities, or occasionally stimulated to overfunction.

Specifically exemplified herein are prophylactic procedures for the prevention or early amelioration of insulin-dependent diabetes (IDD) as a model of a human pathological autoimmunity. Other autoimmune disorders can be addressed with the procedures provided herein. Specific examples of other autoimmune diseases are organ specific autoimmunities, such as multiple sclerosis (MS) and non organ specific autoimmunities, such as rheumatoid arthritis.

The application of the principle of this invention is most advantageous when used to delay or prevent autoimmune diseases that cannot be satisfactorily treated by currently available treatment modalities (e.g., myasthenia gravis), or where the loss of targeted self tissues cannot be compensated for by replacement therapies (e.g., MS) or where replacement therapies provide a means of maintaining life but are unable to prevent long term complications resulting from the disease (e.g., IDD).

A specific embodiment of the subject invention is a novel antigen-driven vaccination regimen for the prevention of IDD. The vaccination procedure involves using infrequent subcutaneous injections of insulin, or fragments thereof, in a composition which further comprises incomplete Freund's adjuvant (IFA). Immunization with subcutaneous insulin in IFA was found to significantly reduce the incidence of IDD in NOD mice. High insulin antibody levels were detected among mice receiving subcutaneous insulin (p<0.001). The protection conferred by subcutaneous insulin immunization was duplicated by immunization with B chain but not A chain insulin fragments. Splenocytes from mice immunized with B chain insulin were able to confer the protective effect on irradiated NOD recipients in adoptive co-transfer studies.

Specifically, we found that NOD mice immunized bimonthly with insulin, suspended in IFA to augment the efficiency of immunization, showed a profound reduction in the frequency of diabetes to under 13% (FIG. 1). This effect was not found following injections to mice of the adjuvant alone (IDD rate of 52%) or to mice given commercial insulin diluent alone (IDD rate of 70%). Similar immunizations with other IDD irrelevant antigens including bovine serum albumin or its specific ABBOS peptide implicated by others (Karjalainen et al. [1992] New Engl. J. Med. 327:302–307) as an important inducer of human IDD had no protective effects. Surprisingly, the severity of the insulitis lesion was not significantly reduced by immunizations with insulin. This demonstrates that the procedure of the subject invention initiates an active favorable immune response which overrides the predisposition to develop IDD. This vaccination therapy is in distinct contrast to previous efforts to prevent IDD by dampening the immune response.

We have further discovered that the protective effect from insulin immunization is specific to unique portions of the insulin molecule. Specifically, immunizing treatments with the A chain of porcine insulin had no protective effects (IDD rate 53%) while all of the protection was localized to the B chain (IDD rate 16%). Immunizations with both A and B chain insulins resulted in high insulin binding activity in serum; however, diabetes was prevented only by B chain immunization. In additional studies, the major epitope involved in the protective effect was found to locate to an 11-amino acid peptide (gly-ser-his-leu-val-glu-ala-leu-tyr-leu-val) (SEQ ID NO. 1) on the B chain. That a hormonally inactive, specific epitope on the insulin molecule could convey the protective effect, suggests that B cell rest is not a factor and that active immunization of lymphocytes is involved. An additional B chain peptide found to have a protective effect is phe-val-asn-gln-his-leu-cys-gly-ser (SEQ ID NO. 2). These two peptides overlap on the insulin B chain. Thus, there appears to be a dominant epitope located on the B chain that induces a protective, antigen-specific, regulatory T cell and idiotype-antiidiotype network, or else the cellular and humoral responses may be dichotomous events.

It would be readily apparent to those skilled in the art with the benefit of the subject disclosure that variants of the peptides and proteins disclosed herein could be used according to the subject invention. For example, insulin protein or peptide sequences from other animals could be used. Also, inconsequential amino acid substitutions could be made which did not affect the ability of the protein or peptide to produce the advantageous protective immune response described herein.

The outstanding protective effect of the subcutaneous insulin and B chain vaccinations of the subject invention was associated with very high circulating levels of antigen-specific antibodies. Such antibodies may be distinct from IAA because of epitope specificity, subclass, or isotype differences and they may therefore also have different biological functions. Thus, these antibodies may competitively antagonize any detrimental effects of IAA They may also stimulate antiidiotypes that bind the IAA and block their potentially harmful effects.

In a further study, splenic lymphocytes from mice immunized with the B chain of insulin were able to protect irradiated, recipient mice co-transferred with spleen cells which otherwise conveyed accelerated diabetes. This strongly suggested that a cell-mediated regulatory action is occurring. Thus, the apparent paradoxical inhibition of autoimmunity by immunization is likely to occur through the stimulation of lymphocyte networks within which immunoregulatory functions predominate and thus actively interfere with the actions of disease-producing clones. Such "suppressive" actions may arise from, for example: (1) release of inhibitory cytokines (e.g., interleukin-10 [IL-10], transforming growth factor-β [TGF-β]), (2) competition for antigen binding between non-destructive and destructive cells recognizing the same antigen, (3) stimulation of "anti-idiotypic" T lymphocytes that bind the TCR of destructive T lymphocytes, and (4) activation of "suppressor-inducer" lymphocytes.

The injection of insulin, or insulin fragments, according to the teachings of the subject invention, is distinct from any previous uses of insulin in several critical aspects. For example, it is of course common practice for individuals with IDD to take daily insulin injections to compensate for the inability of their pancreas to produce sufficient quantities of insulin. By contrast to these daily insulin injections, the procedures of the subject invention would preferably involve a primary immunization followed by periodic boosters. Furthermore, the composition administered according to the subject invention preferably comprises an adjuvant to enhance the immune response. Specifically exemplified herein is the use of incomplete Freund's adjuvant (IFA). Those skilled in the art would appreciate that other adjuvants could be used. Another critical distinguishing feature of the subject invention is the use of insulin immunizations before the appearance of clinical symptoms of IDD. Clearly, because of the metabolic activities of insulin, it is not common practice to administer insulin unless there is already clinical evidence of pancreatic islet cell destruction. According to the subject invention, however, insulin, or a fragment thereof, is best administered before any symptoms appear. In a preferred embodiment, only the B chain of insulin is administered. This procedure is highly advantageous because the B chain does not have, by itself, any metabolic function, yet it is able to confer excellent protection against the subsequent onset of IDD. In addition to the use of insulin to immunize against IDD, other antigens specifically associated with the disease may also be used. The principles exemplified herein with respect to diabetes can be utilized to prevent or ameliorate other autoimmune disorders. Specifically, we have found that antigens associated with particular cells known to be susceptible to autoimmune attack can be used to raise a vigorous, but non-destructive, immune response. An unusual and unexpected aspect of the vigorous immune response elicited by the procedures of the subject invention is the accumulation of lymphocytes at the location of the cells known to be the potential target of the destructive immune response. Despite the infiltration of lymphocytes, the targeted cells are protected against the destructive aspects of the immune response.

The procedures of the subject invention are also unique and advantageous in comparison to reports of oral immunization. Most importantly, the parenteral immunization procedure of the subject invention has been found to be highly effective in preventing the onset of IDD. As shown in FIG. 1, the parenteral administration of insulin, or the B chain of insulin, results in excellent protection against IDD. Oral immunization has not resulted in such levels of protection. It is also clear that the parenteral procedure results in a markedly different immune response, which may well account for the superior results achieved using this procedure. For example, the parenteral procedure claimed here, with its use of an adjuvant, is specifically designed to cause a heightened immune response. Clearly, the augmentation of the immune response is counterintuitive as a means for preventing or alleviating a pathological condition caused by overactivity of a component of the immune system. As exemplified by the EAE model, antigen immunization in the past has been used to produce autoimmune disease. By contrast, oral immunization seeks to directly down-regulate (anergize or deplete) the antigen-specific immune response.

The different immune response to the current invention compared to the response to oral immunization is remarkable. Specifically, we have found that excellent protection is obtained against the progression of autoimmune disease even though there is no reduction in the rate or magnitude of lymphocyte infiltration to the pancreatic islet cell region.

Thus, an immune response still takes place, but the pathogenic aspect of this response has been eliminated or overridden. Other modes of insulin administration, such as oral administration or daily parenteral administration of whole insulin without adjuvant, are known to diminish the infiltration of lymphocytes into the islet cell region. Furthermore, the method of the subject invention raises antibodies which are immunoreactive with insulin. Again, this immune response would not, a priori, be expected to be beneficial in preventing IDD, and such a stimulation of antibody production is not observed with oral insulin treatments.

Since neither insulin nor B chain immunizations diminished insulitis in contrast to that observed after daily subcutaneous insulin treatments in our previous studies, the two protective phenomena appear to involve distinct mechanisms.

Other researchers have attempted antigen-specific therapies in efforts to block the formation of molecular complexes between HLA molecules and T-cell receptors. This can be done, for example, by saturating the body with a competing antigen. This is expected to dampen the immune response through the prevention of cellular and molecular interactions necessary to initiate and carry on the immune reaction. In contrast to these prior efforts aimed at reducing the immune reaction, the current invention is unexpectedly able to utilize a heightened immune response to specifically interfere with the destruction of self tissue.

For example, immunization with human $GAD_{65}$ appears also to be protective in that the onset of diabetes has been delayed. Antigens useful to vaccinate against autoimmune diseases according to the subject invention can be those involved in the pathogenesis of the particular disease for which vaccination is desired. Other antigens may also be used so long as these antigens are associated with the particular cells or tissues targeted by the autoimmune response and they are not found in other locations in the body. Preferably, the antigen will be found in abundance in the organ or tissues targeted by the autoimmune disease. Such treatment will localize the immunoregulatory response to the target organ, thereby allowing paracrine actions of the cells induced by the method of our invention to functionally inactivate the nearby pathogenic cells. In one embodiment of the subject invention, immunization with glucagon is used to protect against diabetes. Although glucagon is associated with the pancreas, it is not involved in the pathogenesis of diabetes. This effect could be mediated by inhibitory cytokines such as interleukin-10 and/or TGF beta. Alternatively, or additionally, antigens involved in the pathogenic process can raise an immune response and participate in that response in a way which specifically eliminates the destructive aspects of that response.

It should also be noted that, to the extent that 64K antigens, as previously described, may include antigens other than GAD, the subject invention can be practiced using immunization with these other 64K antigens or fragments thereof. Such fragments may include, for example, the 37 to 40K fragment. A 50K protein associated with diabetes has also been described.

Table 1 provides specific examples of autoimmune disorders for which the teachings of the subject invention can be applied to design compositions and methods useful in the prevention or amelioration of the autoimmune disorder. In a preferred embodiment, individuals potentially at risk to develop an autoimmune disorder are identified by genetic screening, immunological testing, or other diagnostic procedure. The susceptible individual is then immunized with a composition comprising antigens associated with the specific autoimmune disease. Preferably, the antigen of choice is expressed only by those cells which are targeted by the autoimmune response or are in the same anatomical location as the cells targeted by the autoimmune response. Preferably, the immunizing composition comprises a suitable antigen and an adjuvant which enhances the regulatory aspect of the immune response. The methodology stimulates an immune response which directs lymphocytes to the anatomical location of the targeted cells and, at the same time, protects the targeted cells from any destructive action of the immune response.

TABLE 1

| Disease | Therapeutic Autoantigen |
| --- | --- |
| IDD | Insulin, GAD |
| Multiple sclerosis | Myelin basic protein |
|  | proteolipid protein |
| Autoimmune uveitis (eye disease) | Retinal S-antigen |
| Rheumatoid arthritis | Type II collagen |
| Addison's disease and/or | 21-hydroxylase |
| hypogonadism | 17-hydroxylase |
| Thyroiditis | Thyroglobulin |
|  | thyroid peroxidase |
| Graves' disease | TSH receptor, 64K antigen |
| Atrophic gastritis | Proton pump/ |
|  | $H^+/K^+$ ATPase |
| Myasthenia gravis | Acetylcholine receptor |
| Idiopathic thrombocytopenic purpura | Glycoprotein IIa/IIIb |
| Hemolytic anemia | 95–110 kDa membrane protein |
| Systemic lupus erythematosus | $Sm-D(D_1)$ (snRNP) |
| Primary biliary cirrhosis | 2-oxoacid dehydrogenase family |
|  | sulfite oxidase |
| Wegener's granulomatosis/ polyarteritis nodosa | myeloperoxidase, c-ANCA |
| Inflammatory bowel disease | Target for anti-neutrophil cytoplasmic autoantibody (ANCA) |

Materials and Methods

Animals.

NOD/Uf mice (Winter [1990] *Diabetes* 39:975–982) were bred and maintained in the temperature and light controlled facility of the Department of Pathology at the University of Florida. After weaning at 3–4 weeks of age, littermates were housed in groups of no more than 6 per cage. A soy and fishmeal-based chow (Harlan, Madison, Wis.) and water were available ad libitum. Typical diabetes rates in the NOD/Uf colony at 40 weeks of age are near 90% in females and 30% in males.

Subcutaneous administration of insulin.

Littermates were divided into 3 groups. The first, comprising 23 NOD mice (12 female, 11 male) received 6.25 units (~40 μmoles) of purified porcine NPH insulin, diluted in an equal volume of incomplete Freund's adjuvant (IFA) (Sigma) subcutaneously in multiple injection sites. Complete Freund's adjuvant was avoided because of its known protective effect in NOD mice (Qin et al. [1993] *J. Immunol.* 150:2072–2080). The second group of 22 mice (10 female, 12 male) was injected with diluent for NPH insulin in IFA and the third group of 23 (12 female, 11 male) received diluent fluid alone. Treatments started at 4 weeks of age and subsequent immunizations were administered at ages 12, 16, and 22 weeks. In a second study (see FIG. 1), group 1 (13 females, 10 males) and group 2 (12 females, 11 males) mice were treated as the first 2 groups above except that recombinant human NPH insulin was substituted in group 1 for the porcine insulin preparation originally used. In addition, 2 new treatments were assessed. Group 3 (12 females, 11 males) and group 4 (13 females, 11 males) received recombinant human A chain insulin (105 µg, 40 µmole) and B chain insulin (140 µg, 40 µmoles) respectively. As in the first study, immunizations were given in IFA commencing at 4 weeks of age, but subsequent injections were given at 8 week intervals. In a third NOD mouse experiment, controlled by 18, 0.9% saline+IFA-treated littermates (10 female and 8 male), 18 mice received 250 µg BSA (Sigma) in IFA (10 female and 8 male). A third group of 21 littermates was treated with 100 µg of the 17 amino acid component peptide of BSA called ABBOS in IFA (11 female and 10 male). This peptide has been proposed as an environmental molecular mimic of an endogenous islet protein.
Adoptive transfer.

Thirty female NOD littermates were randomly assigned to receive IFA-containing, subcutaneous immunizations with recombinant human A chain (n=9) or B chain (n=12) insulin, or diluent (n=9) at 4 and 8 weeks of age. At age 10 weeks, splenocyte pools were obtained from these mice, each pool comprising cells from 3 similarly treated animals. These "modulator" splenocytes were mixed with an equal number of pooled splenocytes that had been harvested from 6 untreated, acutely diabetic NOD mice. Six hours after a 700 Rad dose of γ-irradiation, 10 previously untreated, non-diabetic, 10 week old male NOD mice received an intravenous infusion containing a total of $40 \times 10^6$ cells from one of the mixtures, i.e. 3 diluent-, 3 A chain-, and 4 B chain-treated animals.
Monitoring.

Venous blood samples, obtained from the tail vein or retro-orbital sinus were tested serially for glucose and IAA. Blood glucose was determined using a Chemstrip bG (Boehringer Mannheim) read visually as verified by a reflectance meter. Diabetes was diagnosed when the whole blood glucose level was greater than 240 mg/dl (13.3 mmol/L). A liquid phase competitive radiobinding assay using 1:3 diluted mouse sera was used to determine IAA titer (Vardi et al. [1987] *Diabetes* 36:1286–1291). Normal murine levels, established from a survey of 48 mice from six different strains that were not susceptible to spontaneous diabetes were considered to be below 180 nU/ml (3 standard deviations above mean).

Non-diabetic mice in the subcutaneous immunization protocol that survived to 40 weeks were sacrificed at that age. Their pancreata were removed, fixed in 10% formalin and stained for light microscopic examination with hematoxylin and eosin. The slides were coded and a consensus insulitis score was determined by 3 examiners before the code was broken. The presence of insulitis was scored using a previously described dual scale that assesses both the severity of immune infiltration and the cytoarchitectural disruption. Finally, the pancreata from the modulator cell donors in the adoptive transfer studies were similarly reviewed at 10 weeks of age. Pancreata from 8 of 10 recipients (only 2 of 4 mice receiving B chain modulator cells were sacrificed) were analyzed 20 days after their adoptive transfer.
Statistics.

The method of Kaplan and Meier (Kaplan and Meier [1958] *J. Am. Stat. Assoc.* 53:457–481) was used to construct life tables and the logrank Chi-square statistic was used to compare them (Mantel, N. (1966) *Cancer Chemother. Rep.* 50:163–170). A Student t-test or one-way ANOVA was used when appropriate to compare means. Fisher's exact test was applied to compare frequencies in the adoptive transfer studies. P-values are 2-sided.

Following are examples which illustrate procedures, including the best mode, for practicing the invention. These examples should not be construed as limiting. All percentages are by weight and all solvent mixture proportions are by volume unless otherwise noted.

EXAMPLE 1

The Effect of Subcutaneous Insulin

Logrank analysis showed that subcutaneous insulin in IFA significantly reduced the incidence of diabetes in NOD mice (p=0.0002). The mice receiving diluent alone or diluent+IFA developed IDD at similar rates (p=0.3) to those typical for our NOD/Uf colony. When compared to animals treated with diluent in IFA, immunization of animals with the B chain component of insulin in IFA resulted in protection from diabetes. Immunization with A chain insulin did not however alter the course of IDD. Importantly, the life table curves of the animals immunized with either BSA or ABBOS peptide were not different from those of their saline-treated controls.

We also achieved an increase in the incidence and persistence of antibodies to insulin in those animals receiving insulin immunizations. At 12 weeks of age, only 3 of 21 diluent treated and 3 of 23 diluent+IFA treated mice had positive IAA levels detected, while 12 of 21 who received insulin injections were positive for insulin antibodies detected by the RIA binding method (p<0.001). At 26 weeks, insulin antibodies persisted only in the insulin immunized mice. Both the A and B chain immunizations stimulated high levels of insulin antibodies.

Pancreatic histologies were not different among the mice from all 3 original groups who survived to 40 weeks without ever developing diabetes.

EXAMPLE 2

Adoptive Transfer of B Chain Induced Protection

As presented in Table 2, diabetes was transferred within 20 days to 10 week old, irradiated, male NOD recipients by splenocytes from diabetic NOD mice, co-administered with an equal number of splenocytes from animals that had been treated by 2 prior immunizations of diluent (3/3) or A chain (3/3) in IFA. In contrast, diabetes was prevented for at least 75 days (p=0.03) in similar recipients that received co-transfers of splenocytes from B chain treated together with untreated, acutely diabetic mice. The insulitis scores in mice donating splenocytes as well as in recipient mice sacrificed 20 days after transfer were not different among the 3 treatment groups.

TABLE 2

B chain immunization prevents adoptive transfer of IDD

| | Number of Diabetic Mice | | |
|---|---|---|---|
| Treatment | Day 10 | Day 20 | Day 75 |
| Diluent | 0/3 | 3/3 | — |
| A Chain | 0/3 | 3/3 | — |
| B Chain | 0/4 | 0/4* | 0/2** |

*p = 0.03, B chain vs. diluent or B chain vs. A chain.
**B chain-treated mice were sacrificed on day 20 for histological studies.

EXAMPLE 3

Vaccine Compositions

Vaccines for immunizing against an autoimmune condition, in accordance with the teachings of the subject invention, can be prepared by procedures well known in the art. For example, such vaccines can be prepared as injectables, e.g., liquid solutions or suspensions. Solid forms for solution in, or suspension in, a liquid prior to injection also can be prepared. Optionally, the preparation also can be emulsified. The active antigenic ingredient or ingredients can be mixed with excipients which are pharmaceutically acceptable and compatible with the active ingredient. Examples of suitable excipients are water, saline, dextrose, glycerol, ethanol, or the like, and combinations thereof. In addition, if desired, the vaccine can contain minor amounts of auiliary substances such as wetting or emulsifying agents, or pH buffering agents. In a preferred embodiment, adjuvants such as Freund's adjuvant, Freund's incomplete adjuvant, aluminum hydroxide, or muramyl dipeptide or variations thereof are used. Also, cholera toxin subunit B or other agents which stimulate antibody production at mucosal sites can be used. When peptides are used to raise the immune response, the peptides may be coupled to larger molecules such as KLH or tetanus toxoid to enhance immunogenicity. The vaccines are conventionally administered parenterally, by injection, for example, either subcutaneously or intramuscularly.

The compounds can be formulated into the vaccine as neutral or salt forms. Pharmaceutically acceptable salts include the acid addition salts (formed with the free amino groups of the protein or peptide) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The vaccines are administered in a manner compatible with the dosage formulation, and in such amount as will be therapeutically effective and immunogenic. The quantity to be administered can depend on the subject to be treated and the degree of protection desired. Precise amounts of active ingredient required to be administered depend on the judgment of the practitioner and can be peculiar to each individual. However, suitable dosage ranges are of the order of about several hundred micrograms active ingredient per individual. Suitable regimes for initial administration and booster shots are also variable, but are typified by an initial administration followed in one or two week intervals by a subsequent injection or other administration.

EXAMPLE 4

Viral Vaccines

The immunizing compositions of the subject invention may also be administered using a live viral vaccine. Such vaccines are known in the art and are particularly advantageous in delivering an antigen in a prolonged manner. Viral vaccines typically comprise a non-pathogenic virus which has had a heterologous gene, coding for a particular antigen, inserted into the viral genome. As the virus replicates inside the vaccinated host, the foreign antigen is expressed. The host then mounts the desired immune response against the foreign antigen.

The choice of a suitable virus from which to construct a vaccine can be made by a person skilled in the art. Studies with vaccinia virus have demonstrated that poxviruses in general have several advantageous features as vaccine vectors. Poxvirises are taxonomically classified into the family Chordopoxvirinae, whose members infect vertebrate hosts, e.g., the Orthopoxvirus vaccinia. Vaccinia virus has recently been developed as a eukaryotic cloning and expression vector (Mackett, M. et al., [1985] *DNA Cloning*, Vol. II, ed. D. M. Glover, pp. 191–212, Oxford: IRL Press; Panicali, D. et al. [1982] *Proc. Natl. Acad. Sci. USA* 88:5364–5368). Numerous viral antigens have been expressed using vaccinia virus vectors (Paoletti, E. et al. [1986] *Proc. Natl. Acad. Sci. USA* 81:193–197; Piccine, A. et al. [1986] *BioEssays* 5:248–252) including, among others, HBsAg, rabies G protein and the gp120/gp41 of human immunodeficiency virus (HIV). Regulatory sequences from the spruce budworm EPV have been used previously with vaccinia (Yuen, L. et al. [1990] *Virology* 175:427–433).

The advantages of poxviruses as vaccine vectors include the ability of poxyvirus-based vaccines to stimulate both cell-mediated and humoral immunity, minimal cost to mass produce vaccine and the stability of the lyophilized vaccine without refrigeration, ease of administration under non-sterile conditions, and the ability to insert at least 25,000 base pairs of foreign DNA into an infectious recombinant, thereby permitting the simultaneous expression of many antigens from one recombinant.

Viral vaccine formulations may contain appropriate, conventional, carriers or diluents, preservatives, pH adjusters or stabilizers. For example, suitable carriers and diluents include sterile saline, lactose, sucrose, calcium phosphate, gelatin, dextrin, agar, pectin, peanut oil, olive oil, sesame oil, and water. Additionally, the carrier or diluent may include a time delay material, such as glycerol monostearate or glycerol distearate alone or with a wax. In addition, slow release polymer formulations can be used.

A therapeutic composition or vaccine composition of the invention may contain between about $10^1$ to about $10^8$ of the recombinant vaccine. These compositions contain suitable amounts of the active ingredient, the recombinant viral vector containing the antigen, which can be determined by one of skill in the art based upon the level of immune response desired. In general, however, the therapeutic or vaccine composition contains between about $1\times10^5$ to about $1\times10^7$ plaque forming units (PFU) per mL, and more preferably between $1\times10^6$ and $3\times10^6$ PFU/mL.

The therapeutic or vaccine composition of the invention may contain one or more antigens directed to the same or different autoimmune diseases.

A viral vaccine composition of the invention may also contain a suitable adjuvant. The adjuvant is used as a non-specific irritant to attract leukocytes or enhance an immune response. Such adjuvants include, among others, mineral oil and water, aluminum hydroxide, Amphigen, Avridine, L121/squalene, D-lactide-polylactide/glycoside, pluronic plyois, muramyl dipeptide, killed Bordetella, saponins, as Quil A.

Suitable doses of the vaccine composition of the invention can be readily determined by one of skill in the art. Generally, a suitable dose is between 1 to 5 mL of the vaccine composition. Further, the quantity to be administered depends on the size of the host to be treated, the capacity of the host's immune system to synthesize antibodies, the degree of protection desired, and may be adjusted by one of skill in the art. However, suitable dose ranges are of the order of about several hundred micrograms of active ingredient per host.

The therapeutic or vaccine compositions are administered in a manner compatible with the dosage formulation, and such amount as will be therapeutically effective and immunogenic. Typically, the composition can be administered by intradermal scarification using a bifurcated needle analogous to that used for smallpox vaccines. However, any suitable route is acceptable. Preferably, this route is intradermal, intramuscular, or subcutaneous. It is anticipated that a suitable regime for administration is a single treatment.

EXAMPLE 5

BCG Vaccine

An additional vaccination procedure useful according to the subject invention can utilize recombinant attenuated Mycobacterium tuberculin vaccine (BCG) to provide the vehicle for vaccination. As recognized by those skilled in the art, tuberculin can augment the formation of Th2 (T helper 2) cells which secrete interleukins 4 and 10 and TGFβ and augment B cell antibody secretion. These properties can be used advantageously to enhance the creation of antigen-specific regulatory T cells to override the autoimmune process and thereby induce protection.

EXAMPLE 6

Vaccination Programs

Vaccination can be carried out according to the subject invention to provide protection to the general public or to particular individuals believed to be at risk for developing a specific autoimmune disease. For example, in the case of diabetes, children can be screened genetically and through the use of biochemical markers to determine with considerable accuracy the likelihood of a particular child ultimately developing diabetes. Specifically, the prevalence of IDD in the United States is 1 in 300 over a lifetime. Among first degree relatives of affected patients, IDD afflicts an additional 6–10% dependent upon age. One in every 3 identical twin pairs affected by IDD become concordant for the disease. It is also known that one major gene involved in this evident inherited susceptibility is that located at the HLA-DQ locus. DQ human leukocyte antigens, encoded by the short arm of chromosome 6 are heterodimeric molecules which have importance to immunoresponsiveness to specific antigens. Genetics tests are currently being developed which will provide highly accurate information regarding the likelihood of developing IDD. Also, it is well known that persons who have just developed IDD or are in process of developing IDD have a number of disease specific autoantibodies in their blood. Such autoantibodies include those to islet cell antigens (ICA), to beta cell specific proteins of 64 kDa (now thought to be the lower molecular isoform of glutamic acid decarboxylase [$GAD_{65}$]) and of 38 kDa, to native insulin and proinsulin, and to a number of more minor determinants such as carboxypeptidase-H and heat shock proteins belonging to the hsp-60 family. Among unaffected relatives of patients with IDD, the five year predictive value of insulin autoantibodies (IAA) is near 10%, that of ICA approximates 25%, while those having both antibodies have a risk approaching 70%. (Riley et al. [1990] *New Engl. J. Med.* 323:1167–1172; Bonifacio et al. [1990] *Lancet* 335:147–149; Krischer et al. [in press] *J. Clin. Endo. Metab.* Greater predictive risks are associated with antibodies to the 64 kDa antigen (Atkinson et al. [1990] *Lancet* 335:1357–1360). Additional risk can be identified for antibody positive persons who develop an impaired ability to secrete insulin within 3 minutes following a standard intravenous glucose challenge (Robert et al. [1991] *Diabetes Care* 14:718–723). Our research group has also been able to show that these same antibodies can be used to identify those children who are at risk by screening a general population (Maclaren et al. [1985] *Diabetes* 34:97A). This is important, since approximately 85% of all patients with IDD know no other affected relative.

These accurate means of predicting IDD susceptibility can be used as a basis for determining who should be vaccinated according to the subject invention. Additionally, because of the great risk presented by IDD, a vaccination program to immunize all children at an early age can be instituted.

It should be understood that the examples and embodiments described herein are for illustrative purposes only and that various modifications or changes in light thereof will be suggested to persons skilled in the art and are to be included within the spirit and purview of this application and the scope of the appended claims.

We claim:

1. A method for inhibiting autoimmune destruction of pancreatic islet cells, said method comprising the step of nonaerosol, parenteral immunization with a pharmaceutical composition comprising an immunological adjuvant and an antigen, said composition being capable of suppressing the destruction of pancreatic islet cells upon immunization therewith, wherein the antigen in said composition is associated with pancreatic islet cells and is an insulin-dependent diabetes-inhibiting fragment of insulin, said fragment lacking insulin-like metabolic activity of insulin, and wherein said immunological adjuvant is not Freund's complete adjuvant.

2. The method of claim 1 wherein said antigen is either porcine or human.

3. The method of claim 1 wherein said antigen is the B chain of insulin.

4. The method of claim 3 wherein said antigen comprises an amino acid sequence shown in SEQ ID NO:1 or SEQ ID NO:2.

5. The method of claim 1 wherein said adjuvant is Freund's incomplete adjuvant.

6. A pharmaceutical composition for inhibiting the autoimmune destruction of insulin-producing pancreatic cells and for inhibiting and/or preventing onset of insulin-dependent diabetes (IDD), said composition comprising an antigen which is selected from the group consisting of insulin B chain, an insulin-dependent diabetes-inhibiting fragment of insulin and mixtures thereof, wherein said fragment of insulin lacks the insulin-like metabolic activity of insulin, and an immunological adjuvant in a suitable pharmaceutical carrier, wherein said immunological adjuvant is not Freund's complete adjuvant and wherein said composition, parenterally administered in an effective amount, results in the suppression of the autoimmune destruction of insulin-producing pancreatic cells in a mammal susceptible to IDD.

7. The composition of claim 6 in which said antigen comprises the B chain of insulin.

8. The composition of claim 6 in which said antigen comprises the amino acid sequence shown in SEQ ID NO:1 or SEQ ID NO:2.

* * * * *

UNITED STATES PATENT AND TRADEMARK OFFICE
CERTIFICATE OF CORRECTION

PATENT NO. : 5,891,435

DATED : April 6, 1999

INVENTOR(S) : Muir and Maclaren

It is certified that error appears in the above-identified patent and that said Letters Patent is hereby corrected as shown below:

In the Specification:

At col. 4, line 2, rewrite "immunotegulation" as --immunoregulation--.

At col. 7, line 45, insert --.-- immediately after "IAA"

At col. 13, line 12, rewrite "auiliary" as --auxiliary--.

Signed and Sealed this

Seventh Day of September, 1999

Attest:

Q. TODD DICKINSON

Attesting Officer

Acting Commissioner of Patents and Trademarks

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:1:

Gly  Ser  His  Leu  Val  Glu  Ala  Leu  Tyr  Leu  Val
                 5                             1 0

( 2 ) INFORMATION FOR SEQ ID NO:2:

( i ) SEQUENCE CHARACTERISTICS:

```
      ( A ) LENGTH: 9 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:2:

Phe  Val  Asn  Gln  His  Leu  Cys  Gly  Ser
                      5
```